US008185325B2

(12) United States Patent
Nosovitskiy et al.

(10) Patent No.: US 8,185,325 B2
(45) Date of Patent: May 22, 2012

(54) MULTI-FUNCTIONAL, DISCRETE AND MUTUALLY EXCLUSIVE METHOD FOR DETERMINING CONCENTRATIONS OF GASES IN A GASEOUS MIXTURE

(76) Inventors: Pavel Nosovitskiy, Walnut Creek, CA (US); Gennadiy Nosovitskiy, Round Lake, IL (US)

( * ) Notice: Subject to any disclaimer, the term of this patent is extended or adjusted under 35 U.S.C. 154(b) by 519 days.

(21) Appl. No.: 12/322,989

(22) Filed: Feb. 10, 2009

(65) Prior Publication Data

US 2010/0004554 A1    Jan. 7, 2010

Related U.S. Application Data

(60) Provisional application No. 61/065,458, filed on Feb. 11, 2008.

(51) Int. Cl.
*G01N 31/00* (2006.01)
*G11C 17/00* (2006.01)
(52) U.S. Cl. ............................................ 702/24; 365/94
(58) Field of Classification Search ........................ None
See application file for complete search history.

(56) References Cited

U.S. PATENT DOCUMENTS

| | | | |
|---|---|---|---|
| 4,706,493 A | 11/1987 | Chang | |
| 4,941,897 A | 7/1990 | Vann, III | |
| 5,174,044 A | 12/1992 | Jacobs | |
| 5,327,901 A | 7/1994 | Delente | |
| 5,602,326 A | 2/1997 | Takahashi | |
| 6,046,054 A | 4/2000 | McGeelum | |
| 6,076,392 A | 6/2000 | Dizewiecki | |
| 6,128,945 A | 10/2000 | Shioiri | |
| 6,312,390 B1 | 11/2001 | Phillips | |
| 6,540,691 B1 | 4/2003 | Phillips | |
| 6,620,107 B2 | 9/2003 | Payne | |
| 6,673,644 B2 | 1/2004 | Gole | |
| 6,712,770 B2 | 3/2004 | Lin | |
| 6,726,637 B2 | 4/2004 | Phillips | |
| 6,792,793 B2 | 9/2004 | Mendoza | |
| 6,837,095 B2 | 1/2005 | Sunshine et al. | |
| 6,849,239 B2 | 2/2005 | Morris | |
| 6,960,476 B2 | 11/2005 | Morris | |
| 6,974,706 B1 | 12/2005 | Melker | |
| 7,004,909 B1 | 2/2006 | Pattel | |
| 7,076,371 B2 | 7/2006 | Fu | |
| 7,153,272 B2 | 12/2006 | Talton | |
| 7,239,905 B2 | 7/2007 | Kiani-Azarbayjany | |
| 7,248,905 B2 | 7/2007 | Fukuda | |
| 7,308,293 B2 | 12/2007 | Gerlitz | |
| 7,353,152 B2 | 4/2008 | Brazhnik | |
| 7,356,420 B2 | 4/2008 | Vilanova | |
| 7,421,882 B2 | 9/2008 | Leddy | |
| 7,438,855 B2 | 10/2008 | Sota | |
| 7,454,296 B2 | 11/2008 | Wang | |
| 7,460,958 B2 | 12/2008 | Walsh | |
| 7,461,540 B2 | 12/2008 | Monkemoller | |
| 7,473,229 B2 | 1/2009 | Webber | |

OTHER PUBLICATIONS

Ping et al. A novel method for diabetes diagnosis based on electronic nose. Biosensors and Bioelectronics vol. 12, pp. 1031-1036 (1997).*
Comini, E., Fagila, G., and Sberveglieri, G. "Stable and highly sensitive gas sensors based on semiconducting oxide nanobelts." Applied Physics Letters 81.10(2002). New York, NY, US.
Deininger, Williams, and Kostelecky. "Solid State Sensors for Nox Detection." ISA Expo 2003 Technical Conference. Houston, TX, US.
Figaro General Information for TGS Sensors: Technical Information on Usage of TGS sensors for Toxic and Explosive Gas Leak Detectors. Figaro USA Inc, 2004. Glenview, IL, US.
Galeazzo, Peres, Ramirez-Fernandez. "Analysis of Porous Silicon Devices for Gas Sensors." SIM Group, Polytechnic Institute, University of San Paulo, 2001. San Paulo, BR.
Kawi, Li, Gao."Development of Novel Semiconductor Oxide Gas Sensors." PAO Enterprises. 1998. SG.
Loginov, Rembeza, Svistova, and Shcherbakov. "Effect of laser treatment on the gas sensitivity of tin dioxide films." Technical Physics Letters 24.4 (1998): 270-271. New York, NY, US.
Ma, Wang, Liao, Kong. "Study on Sensitivity of Nano-grain ZnO Gas Sensors." Journal of Wide Bandgap Materials 2002:10:113. Thousand Oaks, CA, US.
Rand, Richard. "Lecture Notes on Non-Linear Vibrations." Department of Theoretical and Applied Mechanics. Cornell University. Ithaca, NY, US.
Sakai, Motooka, Miura, and Yamazoe. "Thin-film-type oxide semiconductor sensor for detecting acetone in human expiration aiming at diagnosis of diabetes." Kuyushu University. 1998. Kyushu, JP.
Risby. "Current status of clinical breath analysis." Applied Physics B: Lasers and Optics 85 (2006): 421-26. New York, NY, US.
Harsanyi. "Sensors in Biomedical Applications: Fundamentals, Technology and Applications." CRC Press. 2000. New York, NY, US, pp. 5-8 and 35-40.

* cited by examiner

Primary Examiner — John S Brusca

(74) Attorney, Agent, or Firm — John C. Meline

(57) ABSTRACT

Method and device for detection and quantitative and qualitative analysis of components in a gaseous mixture distinguished by high selectivity and high resolution.
Method allows to distinguish the influence of individual gases, by themselves or in a mixture, on the microstructure of a sensor's sensitive layer and utilizing the variations of measured parameters to analyze and derive the characteristics of gases, for example, the concentration of a gas or multiple gases in a mixture.
As an example, the method could be utilized in medicine for non-invasive detection of the blood glucose level in diabetics. Device realizing the method is described.

17 Claims, 6 Drawing Sheets

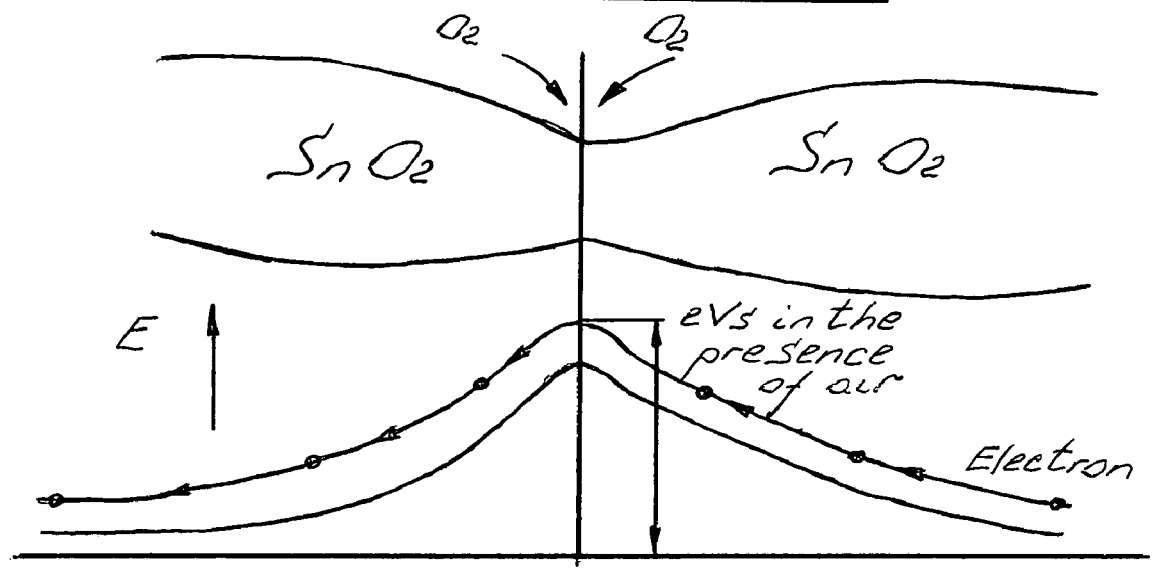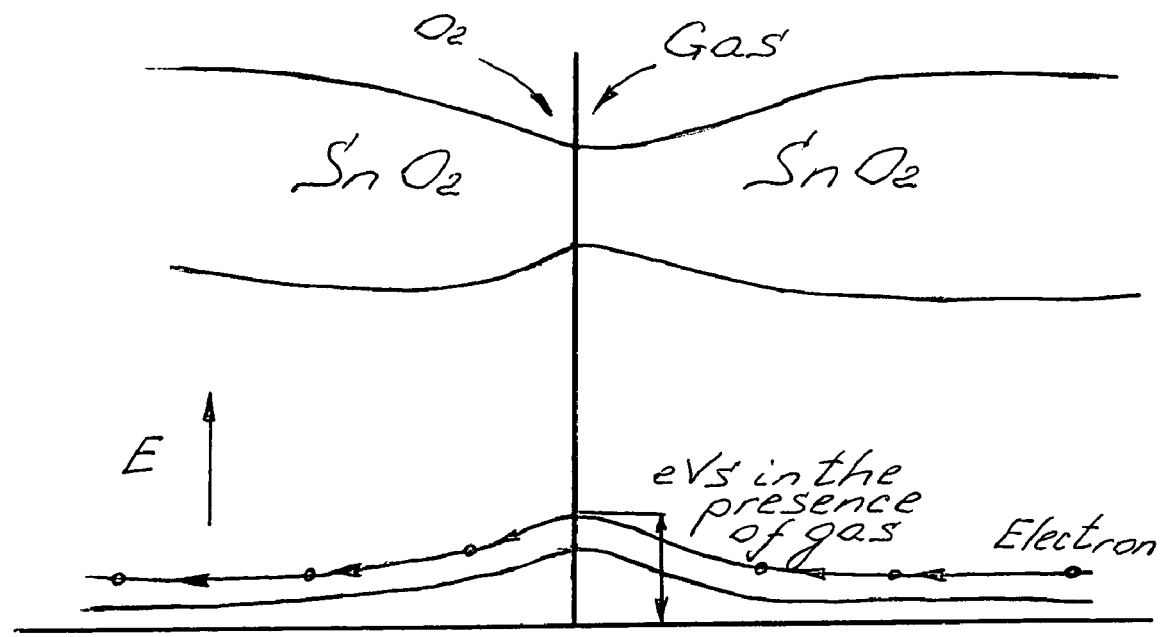

Figure 2:
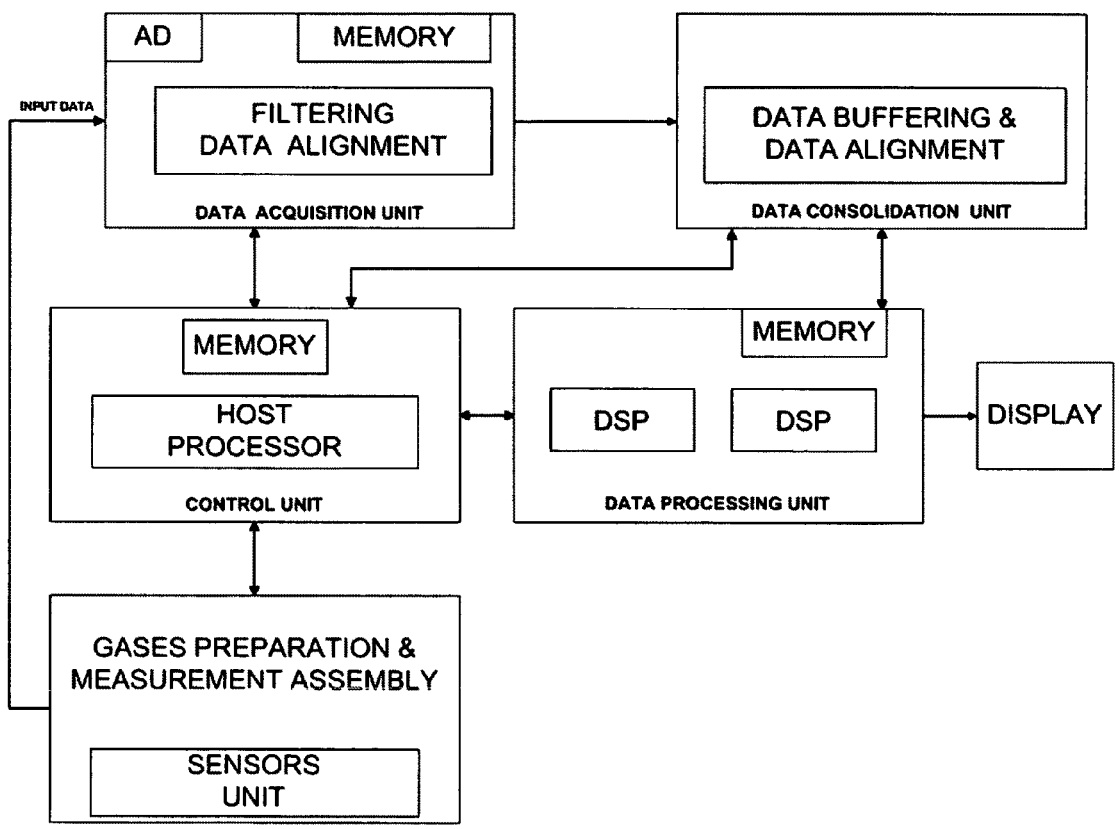

Transition curves in Mathieu's equation. S=stable, U=unstable.

MULTI-FUNCTIONAL, DISCRETE AND MUTUALLY EXCLUSIVE METHOD FOR DETERMINING CONCENTRATIONS OF GASES IN A GASEOUS MIXTURE

I claim priority to the provisional application 61/065,458 filed Nov. 2, 2008.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY REFERENCE OF MATERIAL SUBMITTED ON A COMPACT DISC

Not Applicable

BACKGROUND OF INVENTION

1) Field of the Invention

The invention relates to Measuring and Testing, particularly for Breath Analysis; to Surgery, particularly subclasses for breath analyzing inside the body; to Chemistry, particularly in Analytical and Immunological Testing; to Chemical Apparatuses and Processes; and to Communications. The invention is to be used for gas analysis preferably in medicine, for the defense industry, in the food industry or, in general, to determine quantitative and qualitative characteristics of components in a gaseous mixture with a high degree of selectivity and resolution.

2) Description of Related Art

Currently, a number of marker molecules have been identified in breath that could be used to identify disease, disease progression, or to monitor therapeutic intervention and this list is expected increase dramatically since the analysis of breath is ideally suited for population-based studies in the developed and underdeveloped world.

The concept that blood, urine, and other body fluids and tissues can be collected and analyzed to yield information for diagnosis of disease states or to monitor disease progression and/or therapy is the foundation of modern medicine.

However, the use of breath as a collectable sample has not received comparable clinical use, as conducted studies have only been possible so far as a result of enhanced separation of gaseous molecules by gas chromatography, increased selectivities of mass or optical spectrometers and improved limits of detection from high parts-per-million to parts-per-billion.

Breath measurement has enormous potential, in part because of its inherent safety. The only requirement to collect a breath sample is that the subject must be breathing (spontaneously or mechanically supported). Breath analysis can be used to detect disease, monitor disease progression, or monitor therapy.

Recent advances in instrumentation may enable more of this potential to be realized. In particular, the wider availability of real-time, portable monitors would be a breakthrough. [16]

It was discovered decades ago that atoms and molecules interacting with semiconductor surfaces influence surface properties of semiconductors, such as conductivity and surface potential. Seiyama (1962) and Taguchi (1970) first applied the discovery to gas detection by producing the first chemo-resistive, semiconductor gas sensors. [4] Since then, semiconductor gas sensors have been widely used as domestic and industrial gas detectors for gas-leak alarms, process control, pollution control, etc.

Recent years have seen the introduction of solid state sensors for the detection of different gases, which are based on metal oxide semiconductors. As with catalytic devices, which rely on the absorption of a gas on to a heated oxide surface, the absorption and/or subsequent reaction of a gas on the surface of the oxide produces an electrical conduction change in the metal-oxide itself on the account of the electronic processes involved in the reaction on its surface. [3] [5]

These conductivity changes relate to the amount of gas absorbed on the surface of the oxide and hence to its concentration in the surrounding atmosphere.

The metal-oxide semiconductor sensor is comprised of a tin oxide that is sintered on a small ceramic tube or surface. A coiled wire is placed through the center of the ceramic tube to act as the sensor's heater. Metal wires provide electrical contact between the tin oxide and the rest of the electronics.

The metal-oxide sensor requires between 300 mW and 600 mW of power to operate the sensor at elevated temperature between 300 and 450 degrees Celsius. [2] [3]

The combination of the sensor's operating temperature and the composition of the metal-oxide yields different responses to various gases.

When a metal-oxide crystal, such as $ZnO_2$, is heated at a certain high temperature in the air, oxygen is adsorbed on the crystal surface with a negative charge. Then, the donor electrons in the crystal surface are transferred to the adsorbed oxygen, resulting in a removal of positive charges in a space charge layer. This surface potential is formed to serve as a potential barrier against electron flow. [2-4]

Inside the sensor, electric current flows through the conjunction part (drain boundary) of $ZnO_2$ micro-crystals. At drain boundaries, adsorbed oxygen forms a potential barrier, which prevents carriers from moving freely.

The electrical resistance is attributed to this potential barrier. In the presence of a deoxidizing gas, the surface density of the negatively charged oxygen decreases, thus the barrier height in the drain boundary is reduced. The reduced barrier height decreases the sensor's resistance.

The relationship between the resistance of the sensor and the concentration of the deoxidizing gas can be expressed by the following equation over a certain range of gas concentration: [3]

$$Rs = A[C]^{(-x)} \qquad (1)$$

Where $Rs$=electrical resistance of the sensor
$A$=constant
$[C]$=gas concentration
$(-x)$=slope of the $Rs$ curve.

According to the formula (1), the relationship of the sensor's resistance to gas concentration is linear on a logarithmic scale within a practical range, determined by current market data and depending from the particular gas, to be from approximately a hundred ppm (parts per million) to several thousand ppm of gas concentration. [1]

Modern metal-oxide methods [1], [4], [9], [14] and the method of preparing a sensitive surface with a laser [8] are new, improved, and most closely resembles the method introduced in our invention.

Novel Semiconductor Oxide Gas Sensor was introduced through a research team led by Dr. S. Kawi from the Department of Chemical Engineering NUS. [4] [7] By using new methodology, it is possible to detect relatively lower concentrations (tens ppm) of reducing gases and, with some applied limitations, selectively distinguish certain gases from one another.

The research team has successfully synthesized a novel, high surface area ZnO2 and ZnO2/MCM-41 sensor and developed sensing methods for measuring sensing properties of this material.

The major differences of this method are:
1. A very high surface area of ZnO2 was synthesized using the surfactant synthesis strategy. [7]
2. Higher surface area of ZnO2 translates into the presence of more surface adsorption sites or more surface oxygen anions to be available to react with the reducing gases, producing a larger change in the resistivity of the semiconductor oxide layer.

Another novel method to improve the quality and sensitivity of the ZnO2 layer to tens of ppm is the method of using a laser to scan the sensor's surface. [8] By using a laser, it is possible to change the density of the electrical charge on the sensor's sensitive layer.

For the both described above methods, researchers believe that more extensive experimentation is necessary to understand the nature of the involved processes and create a theory to explain the achieved results.

The described above methods and techniques have several disadvantages in common and cannot be used for investigations of gaseous mixtures with low concentration levels.

The utilization of formula (1) can be limiting and becomes invalid for small concentrations of gas because at low concentration levels, changes in the resistivity also occur under the influence of internal factors, such as diffusion and recombination, which are not taken into account by the formula.

The dependency on a logarithmic relationship derived from the formula (1) does not allow to selectively analyze the affect of similar gaseous components on the semiconductor's sensing layer.

In the presence of destabilizing factors, such as a change in the temperature or a change in the flow of gas, the formula can no longer be applied. Consequently, the destabilizing factors are prevalent at small concentrations.

The advantages and objectives of the proposed invention are as follow:

It is a principal objective and an advantage of the present invention to provide a method to detect, measure and monitor small concentrations of individual gases or gases in a gaseous mixture with high selectivity and high sensitivity.

It is a further objective and an advantage of the present invention to provide an instrument realizing the proposed method to be utilized for various applications, such as the accurate, non-invasive monitoring and diagnostic of pulmonary exclusions.

Other objectives and advantages of the present invention will become obvious in subsequent parts.

BRIEF SUMMARY OF THE INVENTION

The method and device for detection and quantitative and qualitative analysis of components in a gaseous mixture, distinguished by high selectivity and high resolution, allows to discriminate the influence of individual gases, by themselves or in a mixture, on the microstructure of a sensor's sensitive layer and utilizing this influence, analyzes and derives the parameters of the gases, thus bypassing the limitations imposed by traditional measuring and monitoring techniques and creating effective alternatives in areas, such as disease diagnostics in medicine, as well as opening other areas and applications that previously may not have been accessible or attainable in today's practices.

In a second separate aspect of the present invention, the invention consists of a model and the development of a new process for determining the characteristics of various components within gaseous mixtures and involves sensitive and selective measurement of individual gases within the mixture.

In a third separate aspect of the present invention, in accordance with the present invention; the method is distinguished from other methods by high sensitivity and high selectivity and locates domains of dynamic stability and instability.

In a fourth separate aspect of the present invention, the method determines boundaries of the domains of dynamic stability, where measurements can be extracted and domains of instability, where measurements can not be predicted.

In a fifth separate aspect of the present invention, destabilizing factors, such as temperature or pressure fluctuations, which hinder measurements and deform the domains' boundaries, are also taken into account in the analysis.

In a sixth separate aspect of the present invention, that since the domains of stability and instability possess varying widths and can be regulated by changing certain parameters of the system, the method provides the technique to reach desired domains for different applications.

In a seventh aspect of the present invention, relates to an apparatus for measuring gases in a gaseous mixture by implementing the proposed method.

In an eighth separate aspect of the present invention, provides an algorithm, utilizing the above-mentioned method, for the detection of individual components with very similar characteristics in gaseous mixtures through the comparison of locations of individual domains of stability and instability, which are not identical within the measurement diapason.

These and other objectives and features of the present invention will be more fully apparent from the following description and appended claims taken in conjunction with the accompanying figures.

BRIEF DESCRIPTION OF THE SEVERAL VIEWS OF DRAWINGS

FIG. 1: Sensing mechanism in solid state metal-oxide sensors

FIG. 2: Block Diagram of the device for measuring and analyzing exhaled gases based on our novel method FIG. 3: Block Diagram of the Gas Preparation Unit in the device FIG. 4: work of the Measurement Unit with one sensor FIG. 5: shows a block diagram of the Control Unit, which includes the Custom Logic Block. There are subassemblies conforming to an original algorithm to process the gathered information and perform necessary functionalities of the device, thus realizing the proposed method.

Figure 6:
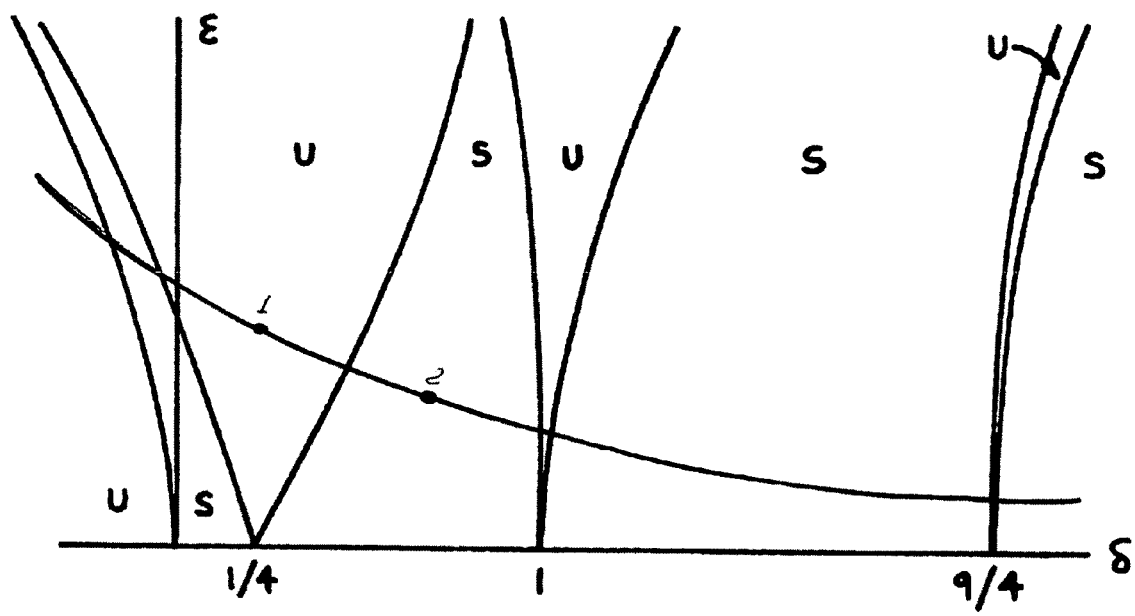

FIG. 6: Transition curves in Mathieu's equations demonstrating areas of stability and instability

DETAILED DESCRIPTION OF THE INVENTION

Today, the function of sensors and the calculation of their parameters are observed during a state of dynamic equilibrium [12], [14], [15]. In a steady state, any small variation or oscillation surrounding the predominant average value are deemed insignificant and are thrown out from the calculation. As a result, limitations occur and sensor's output parameters are only predictable and calculated for a particular range of changing input parameters. For example, sensors work correctly within limited changing characteristics of the sensitive layer under gas influences. Due to the influence of internal factors in the body of the sensor, such as diffusion and recombination, discarding these small changes in relation to the predominant average value is incorrect and produces erroneous results. [11]

Taking into account the periodic changes surrounding the predominant average value of the potential barrier, our derived formula for describing and analyzing the processes in the sensitive layer of a sensor is free from the limitations described above.

$$D^2q/dt^2 - G(Eo-Ex)q = 0 \quad (2)$$

Where q is the charge, G is the conductance constant, Eo is the amplitude of the internal electric field, and Ex is the amplitude of the electric field at the boundary of the microcrystal which prevents carriers from moving freely.

Equation 2 can be simplified to the analysis of the second order differential equation in the following form:

$$D^2q/dt^2 + \text{lambda} * p(t) * q = 0 \quad (3)$$

Where lambda is some constant, p(t) is a function of time which does not greatly vary with its average value. The function p(t), can be then rewritten as:

$$p(t) = \text{alpha}(1 + \text{mu}*f(t)) \quad (4)$$

where alpha and mu are constants and mu<1 and f(t) is a periodic function of t with an angular frequency, omega, for which:

$$\int f(t)dt = 0 \text{ from 0 to omega} \quad (5)$$

If alpha*lambda<0, then at a small enough mu there exists a place of instability.

For alpha*lambda>0 equation (3) can be written in the form below, which describes the range of stability and only in this range can solutions be predicted and calculated.

$$D^2x/dt^2 + \text{lambda}^2 (1+\text{mu}*f(t)) x = 0 \quad (6)$$

The equation above can be solved using numerical approximation methods.

As a result, we determine domains of dynamic stability and instability separated by the occurrence of resonant oscillations, in which the amplitude is raised to detectable levels. (See FIG. 6 and [10])

The following conclusions can be made:
1. Under the influence of flow of gas on the reactive layer of a sensor, the value of the potential barrier does not change gradually with a change in concentration; instead there exist domains of dynamic stability, where parameters can be predicted and domains of dynamic instability, where parameters are unpredictable.
2. Only within domains of stability, it is possible to determine the influence of the external factors to the sensors' sensitive layer.
3. Since the domains of stability and instability possess varying widths, and can be regulated by changing certain parameters of the system, such as temperature, pressure, etc., the method provides the way to determine desired domains for different applications.
4. Measurement procedures within individual areas of dynamic stability can be established and also allow to travel between domains under control of certain parameters and conditions.
5. Comparing the domains of stability and instability for different gases produces the ability to perform selective analysis of the gases in the mixture.
6. The boundaries between zones of dynamic stability and instability can be found by the scanning and detection of increasing amplitudes of oscillations in the diapason of changing measurement parameters.
7. Detrimental factors simply deform the widths of domains of stability and instability without destroying them and are also taken into account in the method.
8. Each gas is described by a differential equation. A gaseous mixture is described by a system of differential equations. The individual equations and the system of equations are solved by conventional methods.

Below is the description for how the device for the proposed method works:

Investigated gaseous mixture, for example the exhaled breath from a patient, is prepared and collected in the Gas Preparation Unit of the device, before processing.

The purpose of the Gas Preparation Unit is to insure that the investigated gaseous mixtures at any time will be measured under equal conditions. The pressure, volume and temperature of the gaseous mixture can vary within the Gas Preparation Unit. All variations are 'regulated with the aid of a microprocessor. Equilibrium, in many cases, must be achieved before processing.

The prepared gaseous mixture is then passed to the Measurement Unit, which serves to determine the concentration of different components in the gaseous mixture.

Internal conditions inside the Measurement Unit, the control and regulation of various parameters, and influences on the process of passing the gases through the sensors, such as air quality, temperature of the sensing layer, speed at which the gaseous mixture is delivered to the sensing layer of the sensor, and the quality of the gaseous mixture itself, are all regulated by the Control Unit, which utilizes the developed algorithm thus realizing the proposed method. The processed gaseous mixture is expelled from the Measuring Unit, preparing the unit for' subsequent measurements.

The Measurement Unit consists of a predetermined number of sensors which react with individual components of the gaseous mixture. The sensors' outputs, a series of analog signals, are then passed to the Data Acquisition Unit for amplification, filtration and digitization by an Analog-to-Digital Converter (ADC). Once digitized, the prepared data is transferred to the Data Consolidation Unit.

The Data Consolidation Unit serves to collect, store, and transfer information from each individual sensor to the microprocessor upon received request. This allows for the consolidation and synchronization of individual subsystems, preventing the loss of data and increasing the dependability at the device;

Data stream then leaves the Data Consolidation Unit directed for processing in the Control Unit. The Control Unit is a major unit, comprised of various subsystems, responsible for performing data conversion, providing internal communication between subsystems and producing necessary commands to accomplish device functionalities.

The DSP based Data Processing Unit functions to perform the actions of the Control Unit and houses the algorithm that controls the work of all subsystems in the device. The Data Processing unit also houses the algorithm to process the gathered data, thus realizing the proposed method. The Data Processing Unit communicates directly with the Control Unit and shares the data produced by the Data Consolidation Unit.

The Control Unit performs, controls, and regulates the functionalities of the device.

The main functions of the Control Unit are:
1) Receives processes, communicates and transfers data to the different units through a common interface. Achieved results are gathered and saved to the database as well as displayed.

2) Controls actions performed by the electro-mechanical modules such as the pump, heater, piston, etc. The Control Unit receives and analyzes the signals from various mechanisms and performs the necessary actions and responses according to built-in application software.

3) Ensures synchronization of electronic blocks and subsystems

The Control Unit is a multifunctional unit, which includes not only standard components, but also contains an original Custom Logic Block. This block has original design circuitries for detecting areas of stability and instability in the changing parameters of the gaseous mixture as predicted by the proposed method. Developed technical solutions for the detection are the subject of patenting the proposed device as well as the proposed method. New circuitries and their functionalities are described below.

Independent modules, measurement tools and/or supplemental devices, when needed, are connected through the interface to the device. The device consisting of original sub-assemblies and application software for calculating, locating and determining the boundaries of domains of stability and instability is described above. It is achieved by analyzing the output data, which reflects the changes in the parameters of the gaseous mixture. Furthermore, the subsystems used in the Control Unit insure reliability and dependability as well as provide ways to troubleshoot and diagnose the device in its entirety.

The major units and their constraints are described below.

Figure 3:
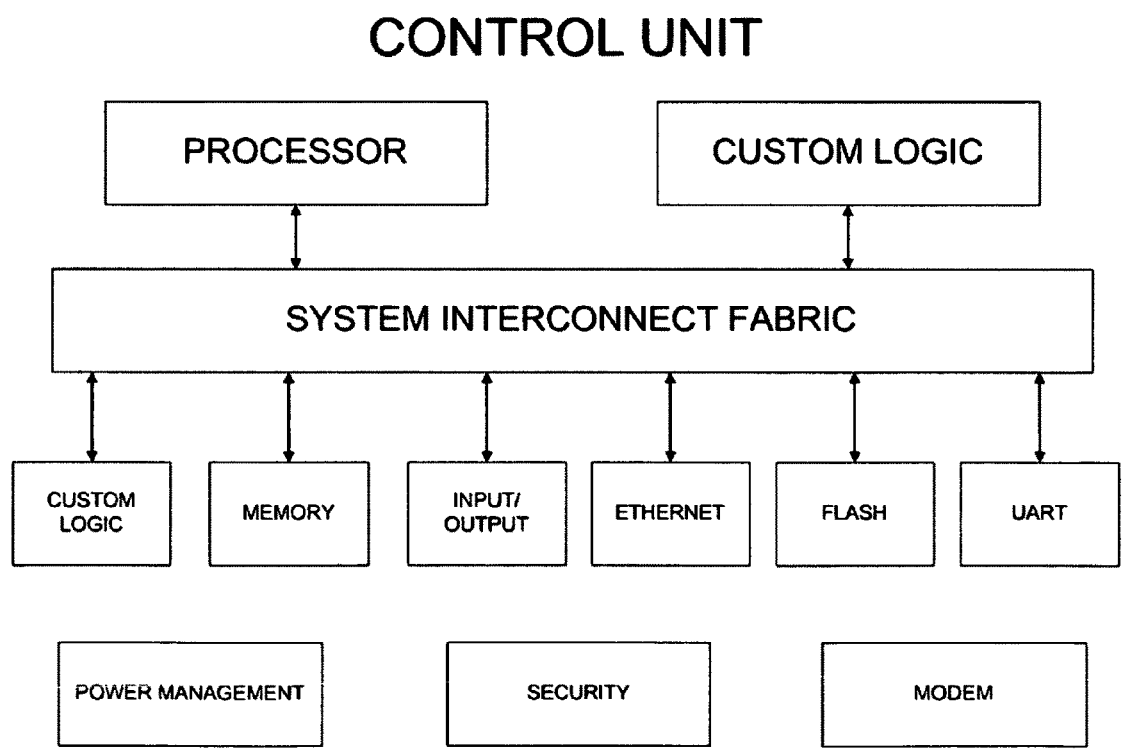

The Gas Preparation Unit works in the following manner:

Gaseous mixture, such as exhaled breath, enters the reservoir through the tube. (FIG. 3)

The pressure and volume of the gaseous mixture is regulated by the change in the position of the piston. The heating element, built into the reservoir, heats the mixture to the assigned temperature.

In the unit, the reservoir consists of two cylinders, one inside the other. The double walls and the inner cavity prevent the exchange of heat with the surroundings. Valve #1 prevents the gaseous mixture from leaving the reservoir. Valve #2 is opened after the prepared gaseous mixture reaches equilibrium, i.e. PV=const at an assigned temperature, allowing the mixture to move into the Measurement Unit for processing. (See FIG. 4 for the Measurement Unit)

The Measurement Unit has a given number of sensors, each of which is configured for the detection of a particular gas. The configuration for the detection of a specific gas requires the heating of the sensitive layer of a sensor to a temperature which corresponds with the temperature at which the specific gas is most active. Each particular gas has its own optimal temperature. Acetone, for example, is most active at 350° C. [7] The heating of the sensing layer of a sensor is achieved through the utilization of an internal, built-in heating element in the sensor.

When the temperature of the sensitive layer of the sensor reaches the assigned value, valve #2 is opened allowing the gaseous mixture to flow onto the sensor. The speed with which the gaseous mixture flows onto the sensing layer, the change of the speed of the gaseous mixture with respect to time, the time the gaseous mixture is in contact with the sensing layer of a sensor and other parameters are regulated.

The gas which has passed through the sensor is collected in the reservoir. This gas can be utilized for further analysis, such as determining the composition of the mixture or simply be released back into the surroundings.

The sensors' output signals—analog signals changing with respect to time—are detected and processed in the electronic subsystems of the proposed device. (See FIGS. 3-5)

The electronic subsystems work in the following manner:

The outputs of the sensors, in form of analog signals, are transferred to the inputs of the Data Acquisition Unit. In the Data Acquisition Unit, signals are amplified, filtered, and' converted to a digital form. Analog-to-Digital Converter is used.

Figure 4:
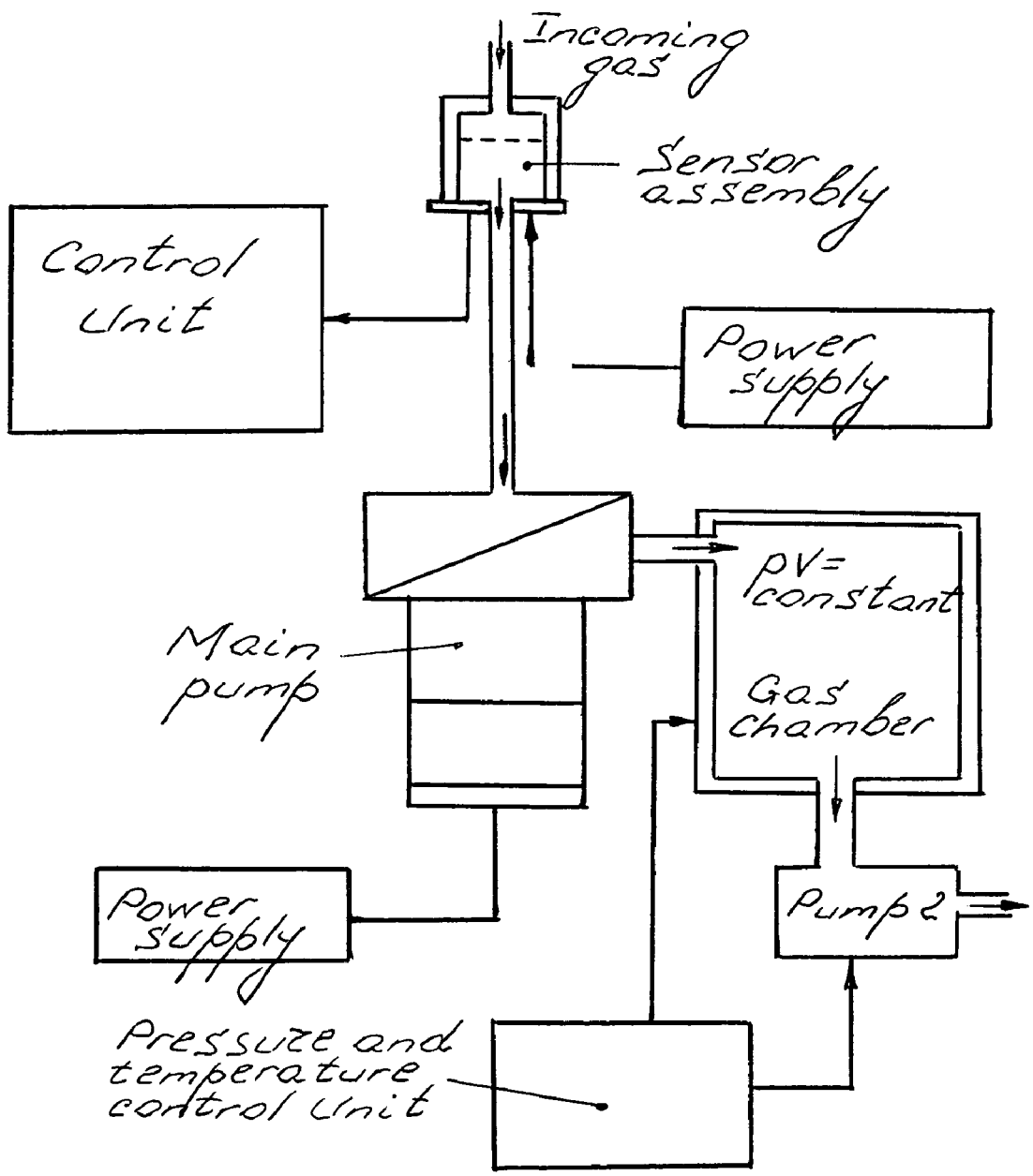
Figure 5:
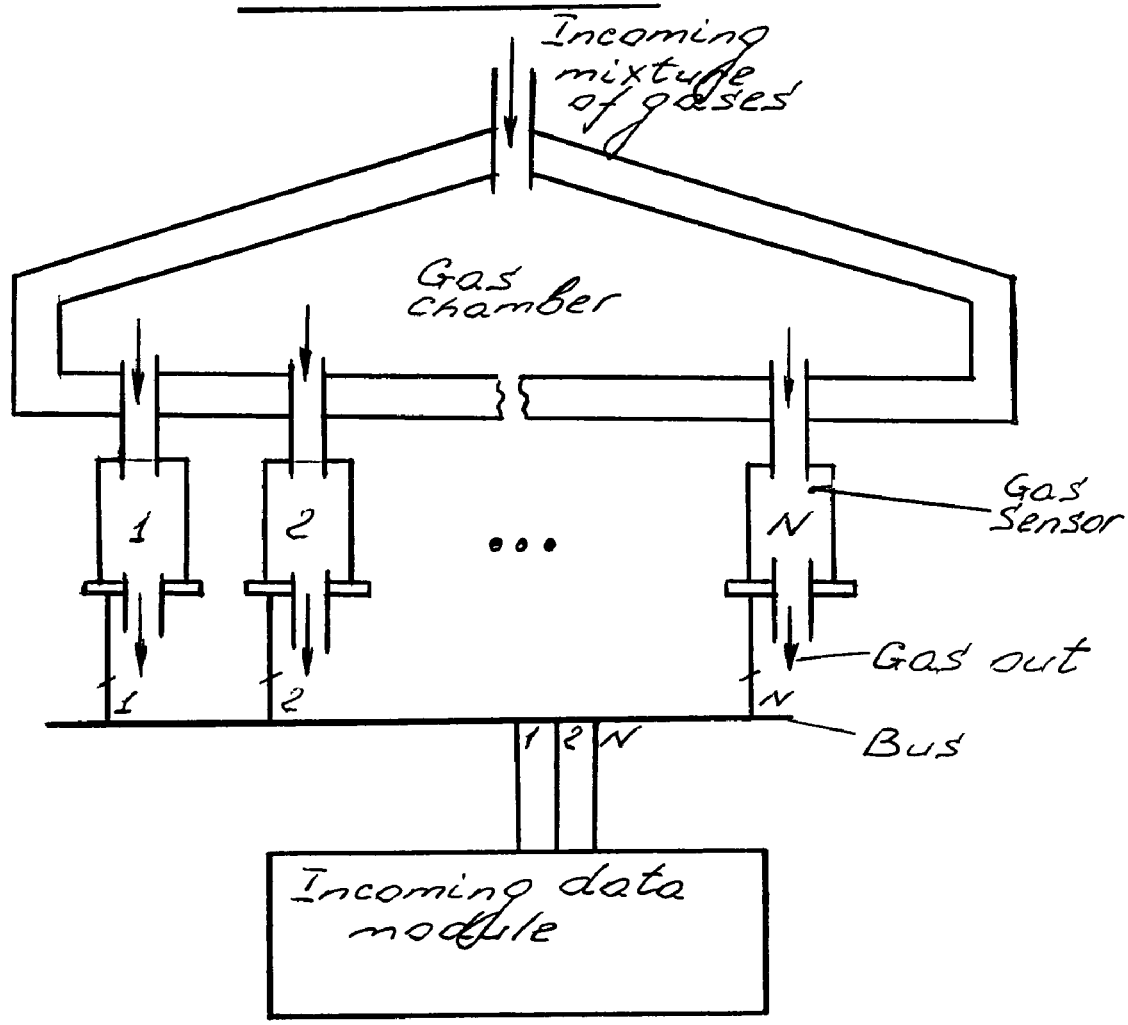

Then the processed signal enters the Data Consolidation Unit where FIFOs and other storage elements are used to save and synchronize the data streams produced inside the internal subsystems. This ensures the functionality and reliability of the processor, the Control Unit and the entire device. The block diagram presented in FIG. 4 provides, as an example, an explanation of the functionalities of a three-channel Data Acquisition and Data Consolidation Units. FIG. 5 shows the structure of the Control Unit, which is responsible for controlling the major processes and functionalities of different components and the device itself, including power distribution, security, mechanical arms control, valve operations, piston movement, etc. The Control Unit also treats and prepares information to be transferred between the internal units.

Original Custom Logic, implemented in the Control Unit, is involved in the detection of the boundaries of stability and instability. Indicated subsystem includes an asynchronous block that operates the application software to determine the domains of stability and instability through the analysis of the changes in the output parameters of the gaseous mixture as outlined by the method. Subsystem also includes time-dependent logic components, switching capacitors and other elements used to determine and analyze the characteristics of oscillation occurring at the boundaries of domains of stability and instability.

The Data Processing Unit contains an implemented algorithm that realizes the proposed method as well as algorithms that utilize proper operations of the device and appropriate software applications to insure continuity, reliability and dependability of the individual subsystems and their interaction within the device. Furthermore, the algorithms define and control the data stream within the device, transferring the data through the interface.

Standard protocols such as UART (serial), TCP/IP and others can be implemented to aid and utilize the information exchange.

What is claimed is:

1. A method for determining a concentration of a component of a sample, the method comprising:
   [1] trapping a volume of the sample in a trapping chamber;
   [2] passing at least a portion of the trapped volume of sample into a sensing chamber, wherein the sensing chamber includes or is in connection with a sensor;
   [3] detecting a change in current as a result of interaction of the sample with a sensor;
   [4] using at least Mathieu's Equation with a value for each of its initial conditions, to determine when a value associated with the detected current is in a stable domain;
   [5] when the value associated with the detected current is not in a stable domain, varying one or more of the initial conditions of Mathieu's Equation, and repeating the determining until the detected current is in a stable domain; and
   [6] determining the concentration of the component of the sample using the value associated with the detected current.

2. The method of claim 1, wherein the sample is a gas.

3. The method of claim 1, wherein the sample is a liquid.

4. The method of claim 1, wherein the value associated with the detected current is a value of the detected current.

5. The method of claim 1, wherein a temperature of the sensor is set to a different temperature from that as used during a previous determining of the concentration of the component of the sample.

6. The method of claim 1, wherein a pressure of the trapped volume of sample is varied from a pressure of the trapped volume of sample as measured during a previous determining of the concentration of the component of the sample.

7. The method of claim 1, wherein Mathieu's Equation is of a form $D^2x/dt^2+lambda^2(1+mu*f(t))x=0$ where lambda represents a numeric constant, where mu represents another numeric constant, and where t represents time.

8. The method of claim 1, wherein the trapping of the volume of the sample in the trapping chamber includes trapping the volume of the sample for a sufficient time so that a substantial portion of the trapped volume of the sample is isolated from an influence of an atmospheric temperature and isolated from an influence of an atmospheric pressure.

9. The method of claim 1, wherein the trapping of the volume of the sample in the trapping chamber includes trapping the volume of the sample sufficiently so as to avoid a measurable amount of contamination.

10. The method of claim 1, wherein a stable domain is a numeric domain where values can be predicted in accordance with the said Mathieu's Equation, and wherein an unstable domain is a numeric domain where a resulting value is unreliable.

11. The method of claim 1, wherein the determining the concentration of the component of the sample includes the use of parametric vibrations when the value associated with the detected current is approximately at a border between a stable domain and an unstable domain.

12. The method of claim 1, wherein the method further comprises using a unique identifier of, or a particular value associated with, the component of the sample to distinguish the component from one or more other components of the sample.

13. The method of claim 1, wherein the sample includes a second component, and wherein the method further comprises:
    performing steps [2] through [5] for the second component; and
    determining the concentration of the second component of the sample using the value associated with the detected current in respect to the second component.

14. The method of claim 1, before using at least Mathieu's Equation, selecting values for the initial conditions for Mathieu's Equation such that when determining the value associated with the detected current is more likely to in a stable domain.

15. A device for detecting a concentration of a component of sample, the device comprising:
    a trapping chamber for containing a volume of the sample;
    a sensing chamber, wherein the sensing chamber includes a sensor, and wherein the sensor is capable of generating a change in current as a result of interaction with the component of the sample;
    a memory configured with instructions to:
        use at least Mathieu's Equation with a value for each of its initial conditions to determine when a value associated with the change in current is in a stable domain;
        when the value associated with the change in current is not in a stable domain, vary one or more of the initial conditions of Mathieu's Equation, and
        trigger a repeating of determining when the value associated with the change in current is in a stable domain; and
    an electrical output to transfer a value associated with the change in current to another component.

16. The device of claim 15, wherein the device further comprises:
    a control unit that is capable of:
        manipulating one or more of the initial conditions of Mathieu's Equation;
        operating the sensing chamber; and
        interact with the memory and electrical output.

17. One or more non-transitory physical computer-readable media configured with instructions for performing a method, the method comprising:
    trapping a volume of the sample in a trapping chamber;
    passing the trapped volume of sample into a sensing chamber, wherein the sensing chamber includes or is in connection with a sensor;
    instructing a processor to detect a value related to a change in current as a result of interaction of the sample with the sensor;
    instructing the processor to perform a calculation using Mathieu's Equation;
    instructing the processor to determine when a value associated with the detected current is in a stable domain;
    when the value associated with the detected current is not in a stable domain, varying one or more of the initial conditions of Mathieu's Equation, and repeating the determining until the detected current is in a stable domain; and
    determining the concentration of the component of the sample.

* * * * *